United States Patent [19]

Paradise et al.

[11] Patent Number: 5,066,489

[45] Date of Patent: Nov. 19, 1991

[54] COMBINATION THERAPY OF IL-2 AND DTIC FOR THE TREATMENT OF MELANOMA

[75] Inventors: Carolyn M. Paradise, Emeryville; Edward C. Bradley, Moraga, both of Calif.

[73] Assignee: Cetus Corporation, Emeryville, Calif.

[21] Appl. No.: 557,203

[22] Filed: Jul. 24, 1990

Related U.S. Application Data

[62] Division of Ser. No. 174,000, Mar. 28, 1988, Pat. No. 4,999,339.

[51] Int. Cl.$^5$ .............................................. A61K 37/02
[52] U.S. Cl. .................................... 424/85.2; 530/351
[58] Field of Search .......................... 530/351; 424/85.2

[56] References Cited

U.S. PATENT DOCUMENTS

| | | | |
|---|---|---|---|
| 4,518,584 | 5/1985 | Mark et al. | 424/85.1 X |
| 4,604,377 | 8/1986 | Fernandes et al. | 530/351 X |
| 4,690,915 | 9/1987 | Rosenberg | 530/351 X |
| 4,766,106 | 8/1988 | Katre et al. | 424/85.2 |

OTHER PUBLICATIONS

Comis, Cancer Treatment Reports, vol. 60, No. 2, 1976.
Dorr et al., Cancer Chemotherapy Handbook, pp. 362–367, 1980, by Elsevier North Holland, Inc. Third Printing (1981).
Roth et al. Current Concepts of Oncology vol. 9(5): 2–11.
Rosenberg et al., The New England Journal of Medicine vol. 316(15): 899–897 (1987).
Salup et al., Cancer Research vol. 46:3358–3363 (1986).
DeVita et al., Cancer Principles & Practice of Oncology 2nd Edition J. B. Lippincott Company (1985) pp. 1405–1408.
Creagan et al., Cancer Treatment Rep vol. 70(5):619–624 (1986).
Roth et al., J Immunol vol. 130:303–308 (1983).
Mule et al., Science vol. 225:1487–1489 (1984).
Cancer Rates and Risks 3rd Edition (1985) NIH Publishing No. 85-691:99–101.
Thurman et al., J. Biol. Resp. Modifiers 5:85–107 (1986).
Legha, Seminars in Oncology 16(1):34–44 (1989).
Stoter et al., Eur J. Cancer Clin. Oncol 25:Supp3 pp. 541–44 (1989).
Shiloni et al., Eur J. Cancer Clin. Oncol. 25:Supp3 pp. 545–549 (1989).
Doyle et al., J. Biol. Response Modifiers 4:96–109 (1985).

*Primary Examiner*—Howard E. Schain
*Attorney, Agent, or Firm*—Philip L. McGarrigle; Lisabeth F. Murphy

[57] ABSTRACT

Therapeutic treatment of malignant melanoma in humans is disclosed wherein a synergistically effective amount of DTIC in combination with IL-2 is administered to an individual having such cancer.

33 Claims, No Drawings

COMBINATION THERAPY OF IL-2 AND DTIC FOR THE TREATMENT OF MELANOMA

CROSS REFERENCE

This present application is a divisional application of U.S. Ser. No. 174,000 filed Mar. 28, 1988, U.S. Pat. No. 4,999,339.

BACKGROUND OF THE INVENTION

1. Field of the Invention

This invention relates to the field of medical treatment. More particularly, this invention is directed to a method for treating malignant melanoma using a combination of IL-2 and DTIC (dimethyl-triazeno-imidazole-carboxmide).

2. Description of Related Art

Melanoma in its advanced stages is an incurable disease. Seventy-five percent of skin cancer deaths in the United States are due to malignant melanoma (Cancer Manual, Sixth Edition, (1982), American Cancer Society, Boston, p. 104). Worldwide, the incidence has been rising sharply doubling, every decade over the past 30 years.

Surgery is the only curative therapy for melanoma in its early stages, although this modality, if used aggressively for local recurrence or metastatic disease to regional nodes, is associated with only a 20-30% cure rate. The role of surgery in advanced diseases is palliative.

Melanoma is considered radioresistant and radiotherapy is used mostly for palliation. Hormonal therapy to date has been disappointing. Chemotherapy has resulted in some partial remissions with a single agent response rate for DTIC of 24% (Roth and Kirkwood (1987) *Curr Top Oncology* 9(5) 2-11). This agent is considered the most effective single agent for the treatment of metastatic melanoma although visceral metastases involving the gastrointestinal tract, the liver, and the brain are relatively less responsive than soft tissue disease.

The hematologic and GI toxicities vary with the DTIC dose regimen used, but antitumor schedule dependency has not been observed. Although not widely studied in melanoma, five-day continuous infusions seem to be a rational compromise with the least acute toxicity and equivalent dose responses. Multidrug combination regimens when compared in randomized prospective trials have not shown statistically significantly better response rates than DTIC alone. (De Vita, V. T., Jr., et al, eds. (1985) CANCER, Principles & Practice of Oncology, 2nd ed., p. 1406).

Although the total spontaneous regression of melanoma has been reported on rare occasions, partial spontaneous regression is a regularly recognized phenomenon. This suggests that an immunologic event occurs with regularity in the disease. Pathologists frequently describe an intense mononuclear cell infiltrate beneath many melanomas suggestive of this immune response (Cancer Rates and Risks, 3rd Ed. (1985), NIH Pub. No. 85-691:99).

Earlier studies using immunotherapy in melanoma have been disappointing. Local immunotherapy with bacille Clamette-Guerin (BCG) showed greatest response in patients with small tumor burdens limited to the dermis. Visceral metastases did not respond and there was, at best, a minor effect on survival. However, much renewed interest in this modality of therapy has been aroused by the discovery of a wide range of immunomodulatory agents. Interferon is in clinical trials and has shown definite but limited efficacy to date (Creagan, E. T., et al (1986) *Cancer Treatment Rep* 70(5):619-624).

For successful specific immunotherapy, the existence of immunogenic tumor associated antigen is required. This is difficult in humans because many human cancers have low immunogenicity. Although there has been some success in preparing melanoma vaccine, some studies have shown that human melanomas only rarely stimulate autologous lymphocytes. The reasons for this lack of stimulatory activity are not well understood. Some investigators have shown a suppression of lymphocyte activity by tumor-derived factors (Roth, J. A., et al (1983) *J Immunol* 130:303-308).

IL-2, a lymphokine that is produced by normal peripheral blood lymphocytes and induces proliferation of antigen- or mitogen-stimulated T-cells after exposure to plant lectins, antigens, or other stimuli, was first described by Morgan, D. A., et al (1976) *Science* 193:1007-1008. In addition to its growth factor properties reported by Morgan et al, IL-2 has been found also to modulate a variety of functions of immune system cells in vitro and in vivo.

IL-2 was initially made by cultivating human peripheral blood lymphocytes (PBL) or other IL-2 producing cell lines. See, for example, U.S. Pat. No. 4,401,756. Recombinant DNA technology has provided an alternative to PBLs and cell lines for producing IL-2. Taniguchi, T., et al (1983) *Nature* 302:305-310 and Devos, R., (1983) *Nucleic Acids Research* 11:4307-4323 have reported cloning the human IL-2 gene and expressing it in microorganisms.

U.S. Pat. No. 4,518,584 describes muteins of IL-2 in which the cysteine normally occurring at position 125 of the wild-type or native molecule has been replaced with a neutral amino acid, such as serine. These muteins possess biological activity. U.S. Pat. No. 4,604,377 issued Aug. 5, 1986 discloses an IL-2 composition suitable for reconstituting in a pharmaceutically acceptable aqueous vehicle composed of oxidized microbially produced recombinant IL-2.

Various therapeutic applications of human IL-2 have been investigated and reported by S. Rosenberg and colleagues (see, for example, Mule, J. J., et al (1984) *Science* 225:1487-1489, Rosenberg, S., et al (1987) *New England Journal of Medicine* 316(15):889-897, and U.S. Pat. No. 4,690,915 issued Sept. 1, 1987).

Combination chemotherapy using two or more anticancer drugs to treat malignant tumors in humans is currently in use in research and in the clinic. However, the reported experience with many of these regimens is modest. Combination chemoimmunotherapy consisting of doxorubicin hydrochloride and recombinant IL-2-stimulated cytotoxic lymphocytes plus recombinant IL-2 (rIL-2) showed promising results in the treatment of murine renal carcinoma (Salup and Wiltrout (1986) *Cancer Res* 76(7):3358-3363).

In light of the seriousness of the disease and the paucity of effective therapeutic agents to treat malignant melanomas, there exists a need to develop a therapeutically effective protocol for treatment of such melanomas.

SUMMARY OF THE INVENTION

The invention is directed to a method for therapeutic treatment of metastatic malignant melanoma in a human patient having melanoma comprising administering to said patient a synergistically effective amount of IL-2 and DTIC.

In preferred aspects of the invention, the IL-2 has substantially the amino acid sequence of mature, native human IL-2, is recombinantly produced from microorganisms, and, further, is a mutein with one or more amino acids of the mature, native human Il-2 sequence changed or deleted to improve the performance or purity of the IL-2.

DESCRIPTION OF THE PREFERRED EMBODIMENTS

Definitions

As used herein, the term "therapeutic" treatment refers to administration of a combination of IL-2 and DTIC to a patient after the patient has been diagnosed as having melanoma.

The treatment is considered therapeutic if, for at least 30 days after treatment, there is at least 50% reduction in tumor mass with no areas increasing in size. The reductions in tumor size must last a minimum of four weeks.

As used herein, the term "synergistically effective amount" as applied to the combination of IL-2 and DTIC refers to the amount of each component which, in combination, is effective for survival of the host and which produces a response rate greater than either DTIC or IL-2 alone. Following convention, the response rate for the number of evaluable patients is the sum total of complete responses (complete disappearance of tumor) and partial responses ($\geq 50\%$ reduction in tumor mass). As applied to the treatment of melanoma, the most promising response rate (%) observed for DTIC alone is approximately 24% (Roth and Kingwood, supra), whereas the most promising response rate (%) observed for IL-2 alone is approximately 31% (Rosenberg et al, 1987, supra).

As used herein, the term "recombinant" refers to IL-2 produced by recombinant DNA techniques wherein generally the gene coding for the IL-2 is cloned by known recombinant DNA technology. For example, the human IL-2 gene is inserted into a suitable DNA vector such as a bacterial plasmid, preferably an E. coli plasmid, to obtain a recombinant plasmid, and the plasmid is used to transform a suitable host. The gene is expressed in the host to produce the recombinant protein. Examples of suitable recombinant plasmids for this purpose include pBR322, pCR1, pMB9 and pSC1. The transformed host may be eucaryotic or procaryotic, including mammalian, yeast, Aspergillus, and insect cells. One preferred embodiment herein, but not the only preferred embodiment, employs bacterial cells as the host.

As used herein, the term "pharmaceutically acceptable" refers to a carrier medium that does not interfere with the effectiveness of the biological activity of the active ingredient(s), is chemically inert, and is not toxic to the human patients to whom it is administered.

As used herein, the term "therapeutic cycle" refers to a 28-day cycle wherein a combination of IL-2 and DTIC is administrated to the patient. Three cycles of this therapy is referred to herein as the "therapeutic regimen." Generally, escalating dosages of IL-2 are administered in each successive cycle. Escalating dosages of IL-2 as used herein, are generally dependent on response and level of toxicity observed for each individual.

MODES OF CARRYING OUT THE INVENTION

The method of this invention involves administering to a human patient a synergistically effective amount of IL-2 and DTIC. IL-2 and DTIC may be administered simultaneously, followed by additional administration of IL-2, or DTIC may be administered individually followed by IL-2 administration.

The administration may take place by any suitable technique, including parenteral administration. Examples of parenteral administration include intravenous, intraarterial, intramuscular, subcutaneous, and intraperitoneal, with intravenous, intramuscular, and subcutaneous administration being preferred, and intravenous being most preferred.

The dose and dosage regimen will depend mainly on the degree of malignancy, the IL-2 (whether modified or not), the patient, the patient's history, and the patient's response to treatment. The amount must be effective to result in clinical improvement or in vitro evidence of immune function augmentation or both. The doses of either compound may be single doses or multiple doses. If multiple doses are employed, as preferred for IL-2, the frequency of administration (schedule) will depend, for example, on the patient, type of tumor response, type of IL-2 dosage amounts, etc. Administration once a week may be effective, whereas for others, daily administration or administration every other day or every third day may be effective. The practitioner will be able to ascertain upon routine experimentation in conjunction with the teaching of the following examples, which route of administration and frequency of administration are most effective in any particular case so as, in every case, to augment cellular immune function in vitro and/or improve clinical signs.

The dosage amount that appears to be most effective herein is one that results in remission, no appearance, or decreased tumor burden and is not toxic or is acceptably toxic to the patient, as defined by the protocol in Example 1 below. Generally, such conditions as fever, chills, and general malaise are considered acceptable. This optimum dose level will depend on many factors, for example, on the type of patient, the response of the patient, the type of tumor, route and schedule of administration, existing tumor burden, the type of IL-2, and the definition of toxicity. Toxicity to the human patient may be defined by the extent and type of side effects, with fever, chills, and general malaise considered acceptable toxicity for purposes herein.

If there is acceptable toxicity and if the route and schedule of administration are intravenous on a weekly basis, the dosage level for each administration of underivatized recombinant, microbially produced IL-2 is preferably at least about 3–13 mg/m$^2$ per week, more preferably, about 5–10 mg/m$^2$ per week, and most preferably about 7 mg/m$^2$ per week.

The dosage levels provided herein have been calculated for IL-2 with a specific activity of $3 \times 10^6$ CETUS units per mg. One CETUS unit equals 2.3 BRMP reference units. It is intended that any IL-2, calibrated to this potency that operates within the designated dosage range, be covered herein.

DTIC is commercially available from Miles Laboratory (Westhaven, Conn.), Merck, Sharp and Dome (Rahway, N.J.) and Lymphomed (Rosemont, Ill.). It is available as a lyophilized drug in 100 and 200 mg ampules without a preservative.

For parenteral administration of DTIC, the drug will also be generally formulated in a unit dosage injectable form (solution or suspension), preferably in a pharmaceutically acceptable carrier medium that is inherently non-toxic and non-therapeutic. Examples of such vehicles include normal saline, sterile water and D5W. The DTIC may contain such substances that enhance isotonicity and add bulk, e.g., buffers and a carrier, such as mannitol. DTIC will typically be formulated at a concentration of about 5 mg/ml to 20 mg/ml, preferably about 10 mg/ml.

For parenteral administration the IL-2 will generally be formulated in a unit dosage injectable form (solution, suspension, or emulsion), preferably in a pharmaceutically acceptable carrier medium that is inherently non-toxic and non-therapeutic. Examples of such vehicles include dextrose solution, mannitol, and normal serum albumin. Non-aqueous vehicles such as fixed oils and ethyl oleate may also be used. The carrier medium may contain minor amounts of additives such as substances that enhance isotonicity and chemical stability, e.g., buffers and preservatives. The IL-2 will typically be formulated in such carriers at a concentration of about 0.1 mg/ml to 100 mg/ml, preferably about 0.1 to 6 mg/ml.

Alternatively, the IL-2 may be made into a sterile, stable, lyophilized formulation in which the purified IL-2 is admixed with a water-soluble carrier such as mannitol, which provides bulk, and a sufficient amount of sodium dodecyl sulfate to ensure the solubility of the recombinant IL-2 in water. The formulation is suitable for reconstitution in aqueous injections for parenteral administration and it is stable and well-tolerated in human patients. The formulation method is more completely described in U.S. Pat. No. 4,604,377 issued Aug. 5, 1986, the disclosure of which is incorporated herein by reference.

As mentioned above, the IL-2 herein may be any IL-2 prepared from tissue cultures or by recombinant techniques, and has substantially the amino acid sequence of any mammalian IL-2, such as, e.g., mouse, rat, rabbit, primate, pig, and human. Preferably the IL-2 has substantially the native, human IL-2 amino acid sequence. More preferably, the IL-2 is recombinant IL-2 with substantially the native, human IL-2 amino acid sequence.

The recombinant IL-2 may be obtained as described by Taniguchi et al (1983) supra, and Devos (1983) supra, by cloning the native human IL-2 gene and expressing it in transformed microorganisms. It may also be an IL-2 mutein as described in U.S. Pat. No. 4,518,584, in which the cysteine normally occurring at position 125 of the wild-type or native molecule has been replaced by a neutral amino acid such as serine or alanine.

Adoptive immunotherapy involves harvesting peripheral lymphocytes by leukophoresis from cancer patients, culturing the cells in vitro in medium containing high doses of IL-2 to induce LAK activity, and reinfusing the LAK cells in conjunction with the administration of IL-2. Studies by Rosenberg et al, *N Eng J Med* (1987), supra have shown promising clinical results with IL-2 and LAK infusions. Considering that adoptive immunotherapy could be easily adapted to the treatment protocols disclosed in the present invention and, that one skilled in the art could easily develop such a protocol, this treatment is intended to be included within the scope of the present invention.

Preferably, the IL-2 is an unglycosylated protein that is produced by a microorganism that has been transformed with the human IL-2 cDNA sequence or a modified human cDNA sequence of IL-2 that encodes a protein with an amino acid sequence at least substantially identical to the amino acid sequence of native human IL-2, including the disulfide bond of the cysteines at positions 58 and 105, and has biological activity that is common to native human IL-2. Substantial identity of amino acid sequences means the sequences are identical or differ by one or more amino acid alterations (deletions, additions, or substitutions) that do not cause an adverse functional dissimilarity between the synthetic protein and native human IL-2. Examples of IL-2 proteins with such properties include those described by Taniguchi et al (1983) supra; by Devos (1983) supra; and by European Patent Publication Nos. 91,539 and 88,195; in U.S. Pat. No. 4,518,584, supra, and in copending U.S. application Ser. No. 893,186, filed Aug. 5, 1986, covering muteins wherein oxidation-susceptible methionine residues are replaced with a neutral or conservative amino acid, such as ala$_{104}$, as well as N-terminal deleted muteins of IL-2 wherein one or more of the first six (1–6) amino acids are deleted. The disclosures of all of these references are incorporated herein by reference.

The hydrophobic recombinant IL-2 produced from certain transformed host cells containing recombinant DNA generally aggregates and/or precipitates inside the cell as opposed to being soluble in the cell culture medium. The intracellularly produced protein must be separated from the cellular debris and recovered from the cell before it can be formulated into a purified biologically active material. European Patent Publication No. 206,828 published Dec. 30, 1986, the entire disclosure of which is incorporated herein by reference, discloses a process for isolating such a refractile material. In this process the cell membrane of the transformed host microorganism is disrupted, greater than 99% by weight of the salts is removed from the disruptate, the desalted disruptate is redisrupted, a material, preferably a sugar such as sucrose, is added to the disruptate to create a density or viscosity gradient in the liquid within the disruptate, and the refractile material is separated from the cellular debris by high-speed centrifugation, i.e., at about 10,000 to 40,000×g. Preferably, the salts are removed from the disruptate by diafiltration or centrifugation and sucrose is added to increase the density of the liquid to about 1.1 to 1.3 g/ml.

After the centrifugation step, the pellet containing the refractile bodies is solubilized with a denaturant such as sodium dodecyl sulfate, the resulting suspension is centrifuged, and the supernatant containing the protein is processed to isolate the protein. The protein is separated from the supernatant by appropriate means such as reverse-phase high pressure liquid chromatography (RP-HPLC) and/or gel filtration chromatography. After such separation, the protein can be processed by disulfide exchange, e.g., using glutathione as described by the following references, the disclosures of all of which are incorporated herein by reference: *Meth Enzym* Vol. 131, Enzyme Structure Part L, C. H. W. Hirs, ed. (Academic Press, Inc., New York, 1986) p.83 (Creighton); Snyder (1987) *Biochemistry* 26:688–694; and Saxena and Wetlaufer, (1970) *Biochemistry* 9:5015.

Alternatively, the separated protein may be oxidized (made to form disulfide bonds) to ensure the production of high yields of recombinant protein in a configuration most like its native counterpart. Such oxidation is described in U.S. Pat. No. 4,530,787 to Shaked, Z., et al., the disclosure of which is incorporated herein by reference. The oxidation may also be carried out by reacting an aqueous solution containing a solubilized form of the protein at a pH between about 5.5 and 9 in the presence of air with at least an effective amount of an oxidation promoter containing a $Cu^{+2}$ cation, as described in U.S. Pat. No. 4,572,798 to Koths, K. et al., the disclosure of which is incorporated herein by reference. The preferred oxidation promoter or oxidant is $CuCl_2$ or (o-phenanthroline)$_2$ $Cu^{+2}$. After oxidation, the protein may optionally be desalted and purified further by RP-HPLC, dilution/diafiltration, S200 gel filtration chromatography, and ultrafiltration techniques before modification with activated homopolymer as described further hereinbelow.

The polymer modification may be carried out at any step after the heterologous IL-2 protein has been isolated in sufficiently pure form to be biologically active for therapeutic purposes. The point at which the modification will occur will depend, for example, on the ultimate purity of the IL-2 required for the final use thereof, including pharmaceutical formulation.

Guanidine hydrochloride may be used as a denaturant for the solubilization of the particle paste or after the HPLC step, as described more fully in copending U.S. patent application Ser. Nos. 48,408 and 48,405, both of which were filed on May 11, 1987, and the disclosures of both of which are incorporated herein by reference.

Preferably, the murein herein is selected from $ser_{125}IL-2$, $ala_{104}ser_{125}IL-2$, $des-ala_1IL-2$, $des-ala_1ala_{104}IL-2$, $des-ala_1ala_{104}ser_{125}IL-2$, $des-ala_1ser_{125}IL-2$, or $ala_{10-4}IL-2$. Most preferably, the IL-2 is the $des-ala_1ser_{125}IL-2$, or $ala_{104}IL-2$. Most preferably, the IL-2 is the $des-ala_1ser_{125}IL-2$ mutein in which the initial terminal alanine is deleted and the cysteine at position 125 is replaced by a serine residue. The IL-2 employed may have at least one or more of the first six N-terminal amino acids of the native IL-2 deleted.

The IL-2 may be purified to clinical purity by the method described in U.S. Pat. No. 4,569,790, issued Feb. 11, 1986, the disclosure of which is incorporated herein by reference.

In an alternative formulation, the recombinant, *E. coli*-produced IL-2 may be chemically modified to increase its solubility and circulating half-life, so that it may be administered less often at lower doses to the patient. For example, copending U.S. application Ser. No. 148,145 filed Jan. 25, 1988 the disclosure of which is incorporated herein by reference, describes solubilizing the IL-2, not by a detergent, but by reacting the IL-2 with an activated polymer selected from polyethylene glycol homopolymers and polyoxyethylated polyols. The polymer is activated by conjugation with a coupling agent having terminal groups reactive with both the free amino or thiol groups of the IL-2 and the hydroxyl group of the polymer. Examples of such coupling agents include hydroxynitrobenzene sulfonic ester, cyanuric acid chloride, and N-hydroxysuccinimide. This modification eliminates the necessity for adding detergents to solubilize the IL-2 at physiological pH. The IL-2 is then formulated directly with the water-soluble carrier and buffer as described above, and the formulation may be lyophilized and the lyophilized mixture reconstituted as described above.

In still another alternative formulation, the recombinant, *E. coli*-produced IL-2 is covalently conjugated to a polyproline molecule through a flexible spacer arm as described in copending U.S. application Ser. No. 931,197 filed Nov. 14, 1986, the disclosure of which is incorporated herein by reference. In still another alternative, the recombinant, *E. coli*-produced IL-2 may be conjugated via at least one of its lysine residues to a heparin fragment having a terminal 2,5-anhydro-D-mannose residue through its aldehyde group, as described by copending U.S. application Ser. No. 879,456 filed June 27, 1986, the disclosure of which is incorporated herein by reference.

When the IL-2 is so modified, administration is expected to be at a dose of between only about $0.18 \times 10^6$ $IU/m^2$ to 3.0 $IU/m^2$ of patient body surface area at least once a week, as opposed to three times a week, due to the increased circulatory half-life of such modified IL-2 over unmodified IL-2.

The various aspects of the invention are further described by the following examples, which are not intended to limit the invention in any manner. In these examples all parts for solids are by weight and all percentages for liquids and gasses are by volume, unless otherwise noted.

EXAMPLES

1. General Treatment Plan

A. Patient Eligibility

Patients, between 18 to 70 years of age, were admitted for three, separate Phase I-II studies. Each patient had to meet the following criteria for entering the study:

1. A histologically confirmed, primary diagnosis of Stage III or Stage IV (disseminated) melanoma.
2. Measurable disease by physical examination or by noninvasive radiologic procedure.
3 A Karnofsky performance score* of 70 or greater.

*Karnofsky Performance Scale

4. Serum creatinine less than 2.0 mg/100 ml; bilirubin less than 1.5 mg/100 ml; SGPT less than 50 IU/L.
5. Granulocyte count greater than 1500/mm$^3$; total WBC count greater than 3000/mm$^3$; platelet count greater than 100,000/mm$^3$; prothrombin time less than 1.3 × control.
6. A minimum life expectancy of four months.
7. The ability to give written informed consent, which must be obtained prior to treatment.

| PERFORMANCE STATUS CRITERIA | |
|---|---|
| ECOG | KARNOFSKY |
| 0 Normal activity | 100 Normal; no complaints |
| 1 Symptoms but ambulatory | 90 Able to carry on normal activities; minor signs or symptoms of disease. |
|  | 80 Normal activity with effort. |
| 2 In bed less than 50% of time | 70 Cares for self. Unable to carry on normal activity or to do active work. |
|  | 60 Ambulatory. Requires some assistance in activities of daily living and self-care. |
| 3 In bed more than 50% of time | 50 Requires considerable assistance and frequent medical care. |
|  | 40 Disabled; requires special |

| PERFORMANCE STATUS CRITERIA | |
|---|---|
| ECOG | KARNOFSKY |
| | care and assistance. |
| 4 100% bedridden | 30 Severely disabled; hospitalization indicated though death not imminent. |
| | 20 Very sick; hospitalization and active supportive treatment. |
| | 10 Moribund |
| | 0 Dead |

Patients with any of the following were excluded from these studies:
1. Serious active infections requiring antibiotic therapy, or other serious intercurrent illness, or past history of any serious opportunistic infections not related to myelosuppressive toxicity.
2. Pregnant or lactating women; women of childbearing potential unless using effective contraception.
3. Participation in another experimental clinical trial within three weeks of entry into the present study.
4. CNS metastases, CNS infection (including retinal disease), vasculitis, a known seizure disorder, or a concurrent malignancy in addition to melanoma.
5. Patients who have received:
   a. Chemotherapy, hormonal therapy, immunotherapy or radiation therapy within three weeks prior to study entry (6 weeks for nitrosoureas or mitomycin C).
   b. Patients who have received DTIC in the past.
6. Patients not considered fully recovered from any prior surgical treatment.
7. Patients with major organ allografts.
8. Patients with history or current evidence of cardiac disease unless they are NY Heart Association Class IA and have a normal stress test.
9. Patients currently participating in another clinical trial (excluding studies using approved antibiotics).

B. IL-2

The recombinant IL-2 employed in these examples was des-ala$_1$ser$_{125}$IL-2. The amino acid sequence of this IL-2 differs from the amino acid sequence of native human IL-2 in that it lacks the initial alanine of the native molecule, and the cysteine at position 125 has been changed to serine. Samples of *E. coli* that produce this IL-2 have been deposited by Cetus Corporation in the American Type Culture Collection, 12301 Parklawn Drive, Rockville, Md., USA on Sept. 26, 1983 under accession number 39,452 and on Mar. 6, 1984 under accession number 39,626 under the provisions of the Budapest Treaty.

The IL-2 was processed and purified as described in the text and FIG. 1 of copending U.S. Ser. No. 715,152 filed Mar. 21, 1985, the disclosure of which is incorporated herein by reference, except that the oxidation was carried out using copper chloride, as described in U.S. Pat. No. 4,572,798 substituted for o-iodosobenzoate. When the IL-2 was recovered from the chromatography step(s), it was lyophilized and resuspended in a neutral aqueous buffer containing the reducing agent (dithiothreitol) to keep the IL-2 in a reduced state and a solubilizing agent to keep it in solution. The purity of the recombinant IL-2 after the chromatography step(s) was at least about 95%, and the IL-2 contained less than about 0.02 ng/ml endotoxin as determined by the Limulus amebocyte assay.

The purified IL-2 was formulated at a concentration of 0.3 mg/ml with 50 mg/ml mannitol.

C. Treatment Protocols

1. Dose and Schedule—Twenty patients received three cycles of Interleukin-2 in combination with DTIC. Each cycle was 28 days in duration. All drugs were administered by hospital staff either while inpatient or in the out-patient clinic. Patients received 1.0 gm/m$^2$ of DTIC as an IV continuous infusion over 24 hours every 4 weeks.

For the First Cycle—Patients were admitted to the hospital on a Sunday evening for a Hickman catheter placement on the succeeding Monday. On Day 1 (Tuesday), DTIC was administered by continuous 24 hour infusion at a dose of 1.0 gm/m$^2$ intravenously. Pharmacokinetic studies were performed on Days 1 and 2. Groups of 3-6 patients initially received IL-2 at 2.0×10$^6$ CETUS units/m$^2$ (0.67 mg/m$^2$) as 30 min infusions on days 15 through 19 and 22-26 of each DTIC cycle.

For the Second Cycle—In the absence of disease progression and Grade III toxicity during cycle 1, the dose of IL-2 was escalated to 3×10$^6$ CETUS units/m$^2$/dose (1.0 mg/m$^2$). IL-2 was again given on days 15-19 and 22-26.

For the Third Cycle—In the absence of disease progression and grade III toxicity, the dose of IL-2 was escalated to 4×10$^6$ CETUS units/m$^2$ (1.33 mg/m$^2$). The dose schedule was identical to that given for cycle two.

Results

DTIC was associated with mild nausea and vomiting in 96% of the courses and required no dosage adjustments for this or for myelosuppression. Dose limiting IL-2 toxicities included fatigue (100%), arthralgias (54%), rigors (54%), hypotension (30%), and depression (23%). Two transient arrhythmias were seen. One patient developed optic neuritis and one patient required overnight hospitalization for hypotension.

DTIC pharmokinetics were performed on the first two cycles in 12 patients. Peak plasma levels of DTIC and AIC (5-aminoimidazole 4-carboxamide), a degradation product of DTIC, were not altered by IL-2.

Of 17 evaluable patients, there were seven partial regressions in liver, lung, bone, and lymph node. Lymphocyte counts, T-cell subsets, NK and LAK assays, and IL-2 antibodies were also measured.

In summary, the combination of DTIC and IL-2 was well-tolerated and produced encouraging responses, particularly in visceral sites and bone, areas normally unresponsive to treatment with DTIC.

Duration of Therapy

Patients who had achieved a complete response upon completion of the first three cycles may repeat an additional two cycles beyond documentation of response and then be observed for duration of response.

Patients who had a partial response upon completion of the first three cycles of therapy may continue therapy until complete response occurs or until disease progression or toxicity intervenes. If a complete response is achieved, they may repeat an additional two cycles beyond documentation of response and then be observed for duration of response.

2. Dose and Schedule

Patients will receive three cycles of IL-2 in combination with DTIC. Each cycle is 28 days in duration. For the first administration of IL-2, and for the first dose in the event of dose escalation, patients are observed in the clinic for at least four hours following IL-2 administration. Patients will receive DTIC 200 mg/m$^2$/d × five days every four weeks as a continuous infusion.

- Cycle 1—DTIC 200 mg/m$^2$/d is administered as a continuous infusion on Days 1–5 simultaneously with IL-2 therapy. Patients receive daily intravenous rapid bolus infusions of 2×10$^6$ CETUS units/m$^2$ of IL-2 for five consecutive days per week (Monday to Friday) for two weeks, (Days 1–5 and 8–12) during the first and second weeks of the cycle. No IL-2 is administered during weeks 3 and 4.
- Cycle 2—DTIC is again given as stated above on Monday through Friday, Days 1–5. Patients continue to receive daily (M-F) bolus infusions of IL-2 for two weeks, Days 1–5, 8–12. In the absence of Grade III toxicity or sufficient disease progression to remove the patient from study during Cycle 1, the dose of IL-2 is escalated to 4×10$^6$ CETUS units/m$^2$/dose, during the first and second weeks of the cycle. No IL-2 is administered during weeks 3 and 4.
- Cycle 3—DTIC is again given on Days 1–5. Patients continue to receive daily (M-F) rapid bolus infusions of IL-2 for two weeks, Days 1–5, 8–12. In the absence of Grade III toxicity or disease progression sufficient to remove the patient from the study during Cycle 2, the dose of IL-2 is escalated to 6×10$^6$ CETUS units/m$^2$. No dose escalation beyond 6×10$^6$ units/m$^2$ dose is made.

Patients who have progressive disease or no change upon completion of the first three cycles are removed from the study.

Duration of Therapy

Patients who have achieved a complete response upon completion of the first three cycles may repeat an additional two cycles beyond documentation of response and then be observed for duration of response.

Patients who have a minor or partial response upon completion of the first three cycles of therapy may continue therapy until complete response occurs or until disease progression or toxicity intervenes. If a complete response is achieved, they may repeat an additional two cycles beyond documentation of response and then be observed for duration of response. If the response becomes stabilized without a complete response being achieved, patients will be removed from active treatment but continued on study until disease progression.

3. Dose and Schedule

Patients will receive three cycles of IL-2 in combination with DTIC. Patients receive DTIC 250 mg/m$^2$ daily IV infusion (over one hour) M-F of week 1 of each cycle. IL-2 is administered as an IV bolus injection on M-W-F of each week. The dose of IL-2 is 6×10$^6$ CETUS units/m$^2$ (2 mg/m$^2$). A test dose of IL-2 (2×10$^6$ CETUS units/m$^2$) on Day 1 of the first cycle is given to each patient. If there are no significant adverse effects the next dose of IL-2 is at 6×10$^6$ CETUS units/m$^2$.

Modifications of the above-described modes of carrying out the invention that are obvious to those skilled in the fields of molecular and clinical biology, pharmacology, and related fields are intended to be within the scope of the following claims.

What is claimed is:

1. A method for the therapeutic treatment of melanoma in a human patient having said disease comprising parenterally administering to said patient a synergistic combination of IL-2 and DTIC effective to cause regression of the melanoma.
2. The method of claim 1 wherein the IL-2 is a mutein.
3. The method of claim 2 wherein the mutein has a serine or alanine residue at position 125, numbered in accordance with the mature, human native sequence.
4. The method of claim 3 wherein the mutein has no alanine residue at position 1, numbered in accordance with the mature, human native sequence.
5. The method of claim 4 wherein the mutein has a serine or alanine residue at position 104 numbered in accordance with the mature, human native sequence.
6. The method of claim 2 wherein the mutein is des-ala$_1$IL-2, des-ala$_1$ala$_{104}$IL-2, des-ala$_1$ala$_{104}$ser$_{125}$IL-2, des-ala$_1$ser$_{125}$IL-2, ala$_{104}$IL-2, ser$_{125}$IL-2, or ala$_{104}$ser$_{125}$IL-2.
7. The method of claim 1 wherein the IL-2 is chemically modified to increase its solubility and circulating half-life.
8. The method of claim 7 wherein the IL-2 is covalently conjugated to a homopolymer of polyethylene glycol, polyproline, a heparin fragment, or a polyoxyethylated polyol, wherein the polyethylene glycol homopolymer may be unsubstituted or substituted with an alkyl group on one end.
9. The method of claim 1 wherein IL-2 and DTIC are each administered by intravenous infusion.
10. The method of claim 1 wherein IL-2 is administered in an amount of about 5–10 mg/m$^2$ per week.
11. The method of claim 1 wherein DTIC is administered in an amount of about 750–1300 mg/m$^2$ per week.
12. The method of claim 1 wherein the administration of DTIC precedes the administration of IL-2.
13. The method of claim 12 wherein about 1.0 gm/m$^2$ DTIC is administered by intravenous infusion at day 1 of a therapeutic cycle.
14. The method of claim 12 wherein DTIC is administered by intravenous infusions of about 200–250 mg/m$^2$ per day for five days.
15. The method of claim 12 wherein IL-2 of about 0.5 to 1.5 mg/m$^2$ per day is administered by intravenous bolus infusions for five days.
16. The method of claim 15 wherein escalating dosages if IL-2 are administered per successive therapeutic cycle.
17. The method of claim 16 wherein the concentration of IL-2 is about 0.5 to about 0.7 mg/m$^2$ per day in the first cycle.
18. The method of claim 16 wherein the concentration of IL-2 is about 0.5 to about 1.0 mg/m$^2$ per day in the second cycle.
19. The method of claim 16 wherein the concentration of IL-2 is about 0.7 to about 1.5 mg/mm$^2$ per day in third cycle.
20. The method of claim 15 wherein IL-2 administration is begun at week 3 of the therapeutic cycle.
21. The method of claim 15 wherein IL-2 administration is repeated at week 4 of the therapeutic cycle.
22. The method of claim 1 wherein the administration of IL-2 precedes the administration of DTIC.

23. The method of claim 22 wherein IL-2 of about 5–10 mg/m² per week is administered by intravenous infusion.

24. The method of claim 23 wherein IL-2 administration is repeated in week 2 of the therapeutic cycle.

25. The method of claim 22 wherein about 1.0 gm/m² DTIC is administered by intravenous infusion during week 3 of the therapeutic cycle.

26. The method of claim 1 wherein IL-2 and DTIC are administered concurrently.

27. The method of claim 26 wherein DTIC is administered by intravenous infusions of about 200–250 gm/m² per day for five days.

28. The method of claim 26 wherein IL-2 of about 0.5–2 gm/m² per day is administered by intravenous infusions for five days.

29. The method of claim 28 wherein escalating dosages of IL-2 are administered per successive therapeutic cycle.

30. The method of claim 28 wherein IL-2 administration is repeated in week 2 of the therapeutic cycle.

31. The method of claim 26 wherein IL-2 is administered three times per week throughout the therapeutic cycle.

32. The method of claim 31 wherein the weekly amount of IL-2 is 6 gm/m², administered in three equal dosages of 2 gm/m².

33. The method of claim 1 wherein the IL-2 has substantially the amino acid sequence of native, human IL-2 and is produced by recombinant DNA technology.

* * * * *